United States Patent
Lin

(10) Patent No.: US 9,339,196 B2
(45) Date of Patent: May 17, 2016

(54) NON-INVASIVE METHOD AND DEVICE OF MEASURING THE REAL-TIME CONTINUOUS PRESSURE OF FLUID IN ELASTIC TUBE AND THE DYNAMIC COMPLIANCE OF ELASTIC TUBE

(71) Applicant: GONG BU DESIGN COMPANY, Taichung (TW)

(72) Inventor: Albert Chin-Yuh Lin, Taichung (TW)

(73) Assignee: Gong Bu Design Company, Taichung (TW)

( * ) Notice: Subject to any disclaimer, the term of this patent is extended or adjusted under 35 U.S.C. 154(b) by 559 days.

(21) Appl. No.: 13/826,470

(22) Filed: Mar. 14, 2013

(65) Prior Publication Data

US 2014/0276134 A1    Sep. 18, 2014

(51) Int. Cl.
   *A61B 5/02*     (2006.01)
   *A61B 5/021*    (2006.01)
   *A61B 5/00*     (2006.01)

(52) U.S. Cl.
   CPC ............. *A61B 5/021* (2013.01); *A61B 5/02007* (2013.01); *A61B 5/6843* (2013.01)

(58) Field of Classification Search
   USPC ........................... 600/485, 486, 301, 306, 490
   See application file for complete search history.

(56) References Cited

U.S. PATENT DOCUMENTS

2009/0069699 A1*  3/2009  Lin ...................... A61B 5/6843
                                                600/485

OTHER PUBLICATIONS

A. C-Y. Lin et al., "On measuring the instantaneous blood pressure in an artery via the tissue control method," Jul. 30, 2007, Physiol Meas 28, 2007, 937-951 (Lin).*
Lab #6 for Geophysical Inverse Theory ESS523, Fall 2005, Univ. of WA TA presenting this lecture : Andy Ganse Course professor : Ken Creager, Nov. 22, 2005 (Ganse).*

\* cited by examiner

*Primary Examiner* — Michael Kahelin
*Assistant Examiner* — Mitchell E Alter
(74) *Attorney, Agent, or Firm* — Rosenberg, Klein & Lee

(57) ABSTRACT

The invention presents a non-invasive method and device of measuring the real-time continuous pressure of fluid fluctuating in an elastic tube and the dynamic compliance of the elastic tube, in which the theory of VLDT (Vascular Loading Decoupling Technique) is used. After searching the initial critical depth and determining the decoupled ratio, a DC controller generates a DC control gain to maintain the elastic tube at critical depth, and an AC controller employs the self-adaptive and Step-Hold control rules to create the pulsation of elastic tube without effect of surrounding tissues, and be capable of measuring the real-time continuous fluid pressure and dynamic compliance of elastic tube.

4 Claims, 11 Drawing Sheets

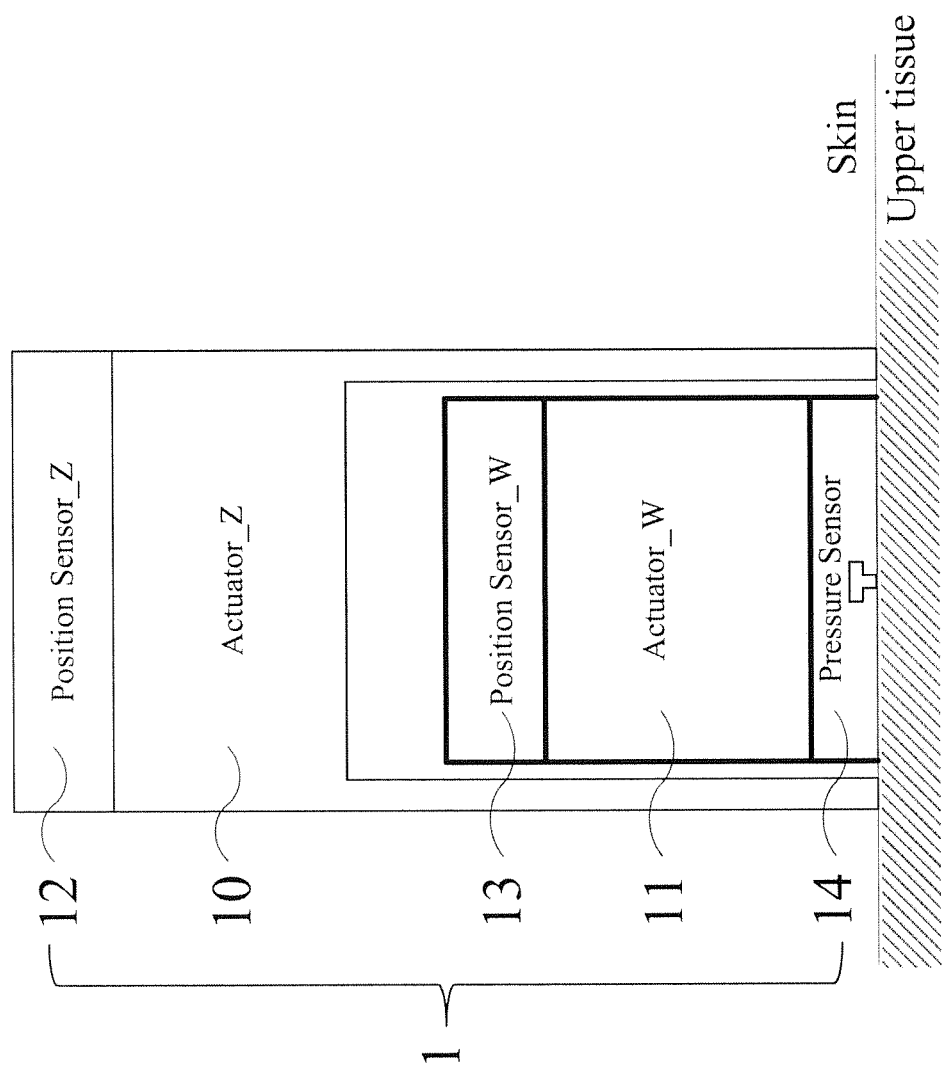

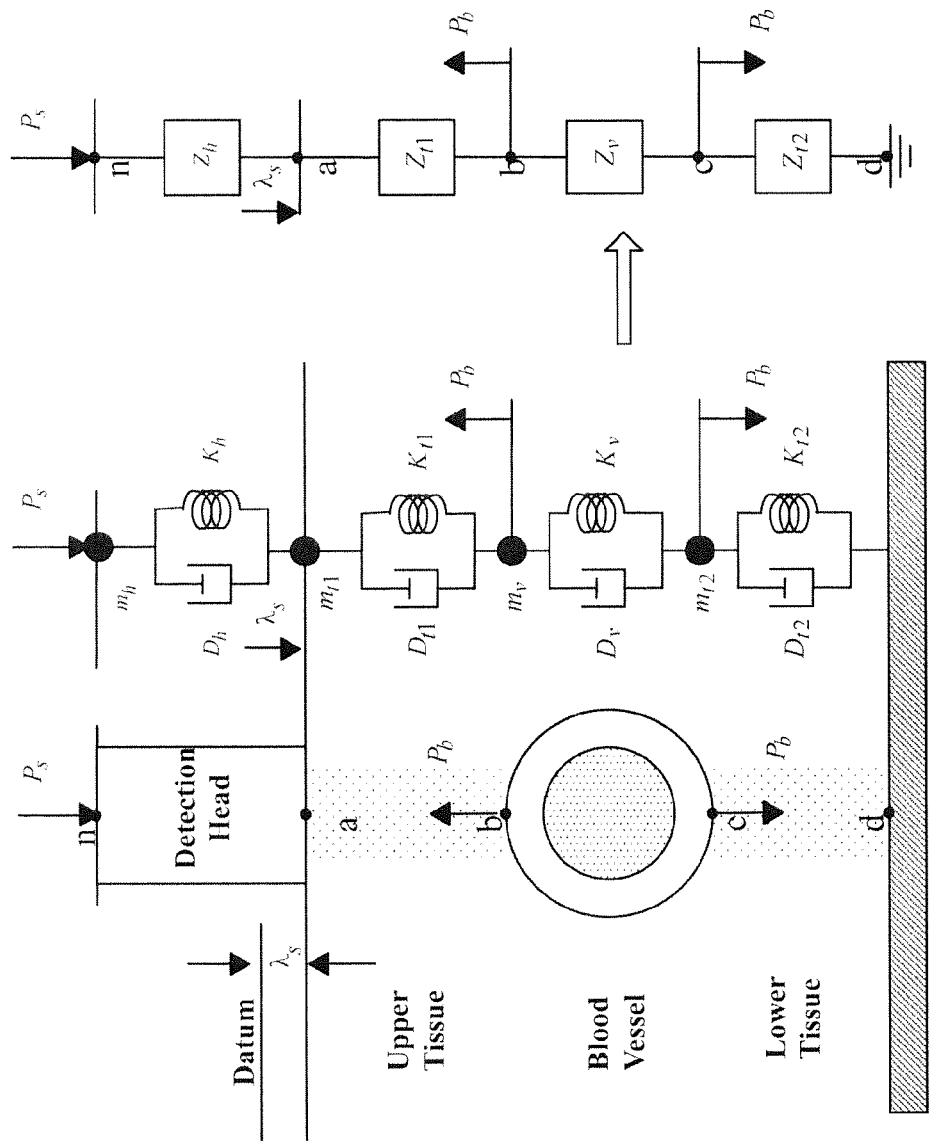

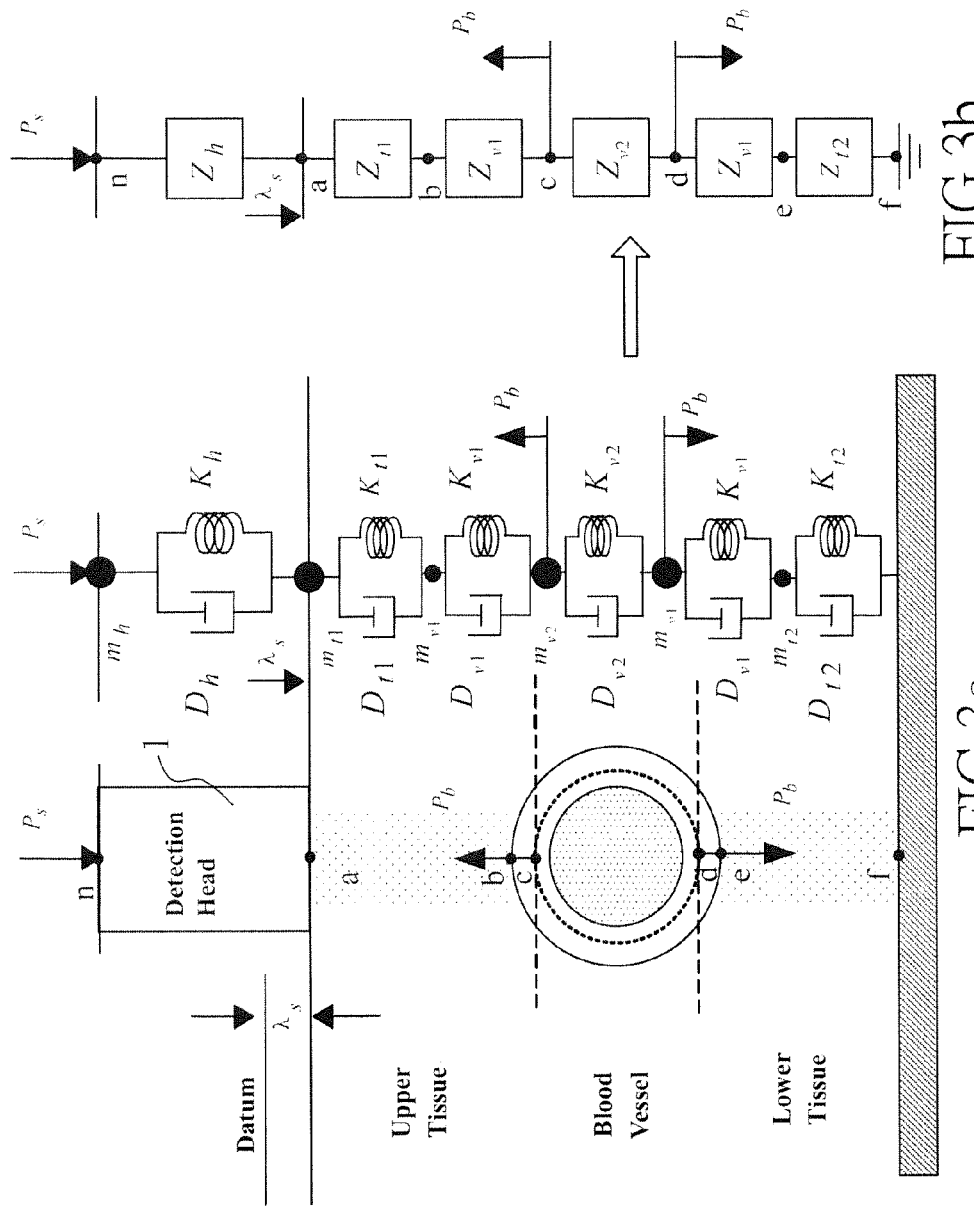

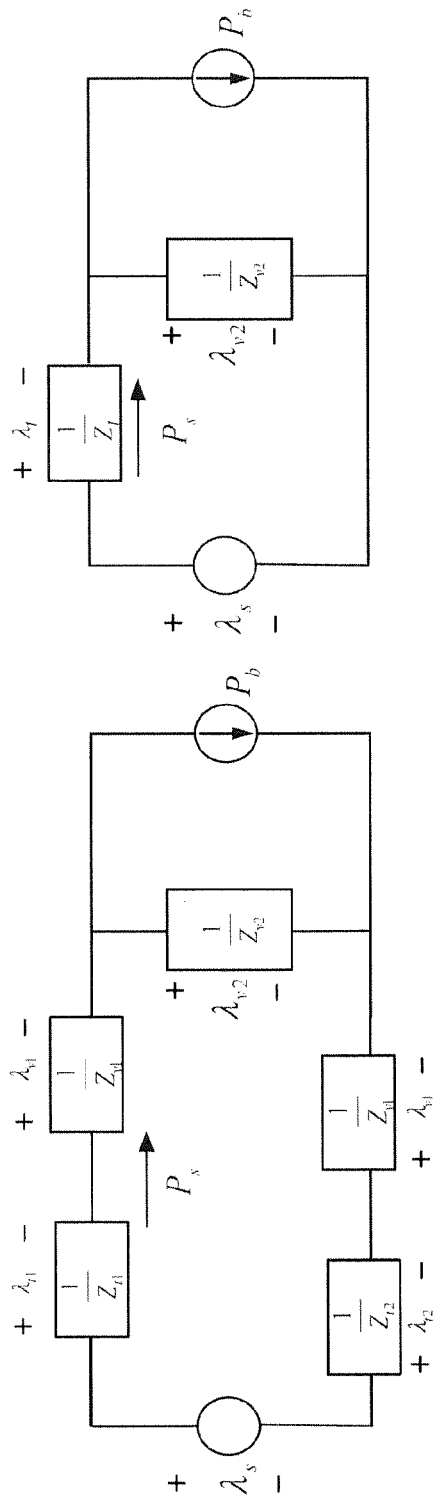
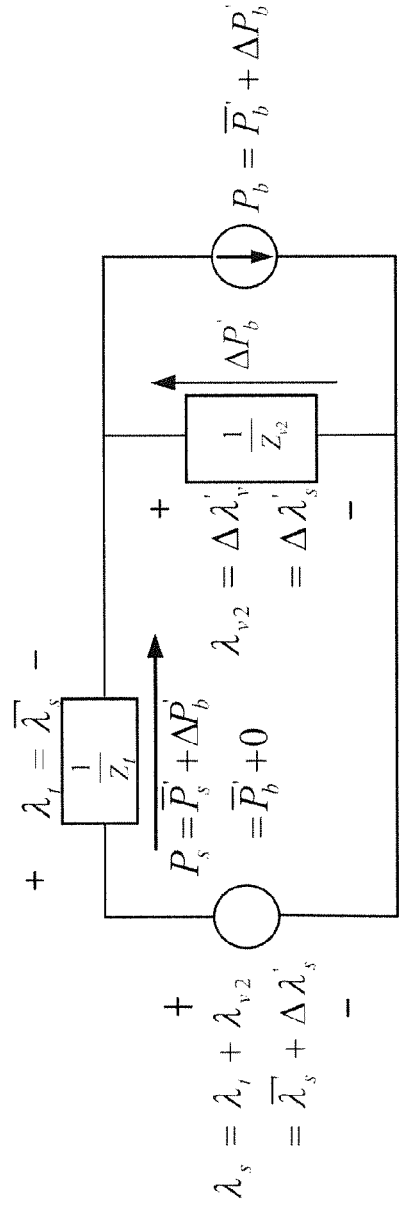
FIG.3c
FIG.3d
FIG.3e

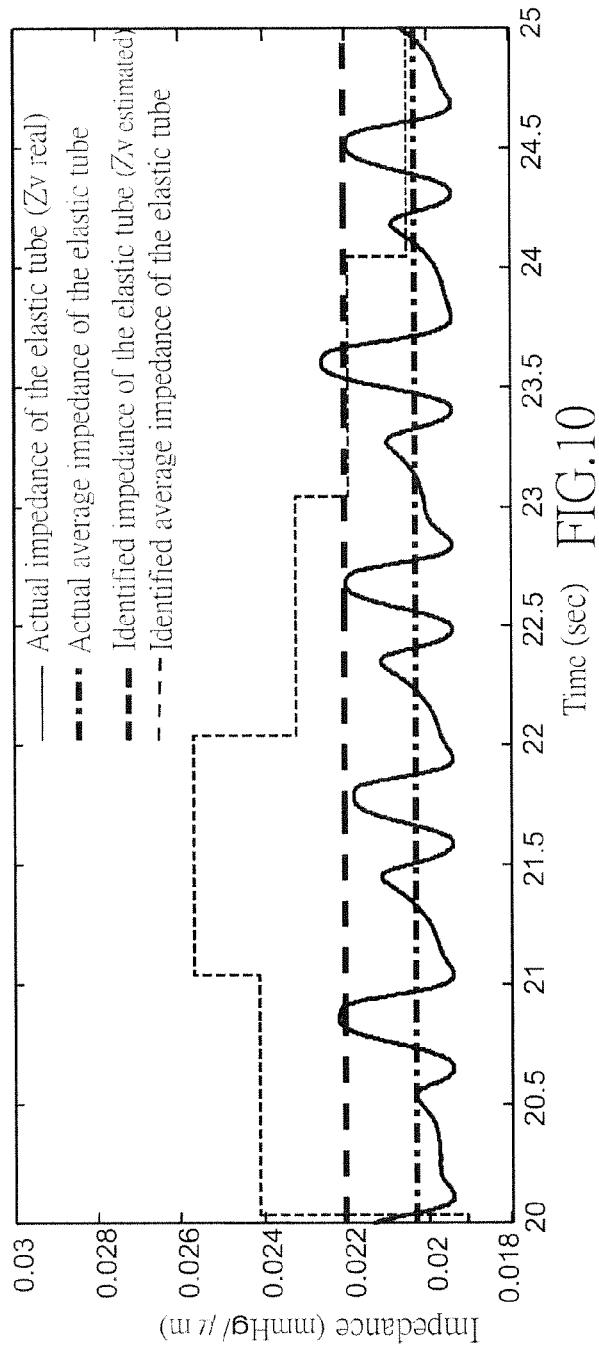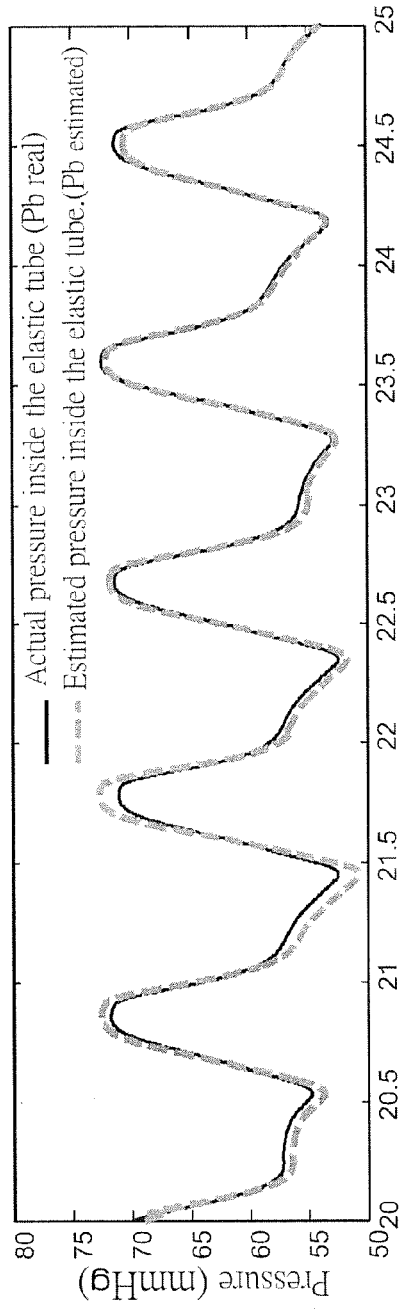

NON-INVASIVE METHOD AND DEVICE OF MEASURING THE REAL-TIME CONTINUOUS PRESSURE OF FLUID IN ELASTIC TUBE AND THE DYNAMIC COMPLIANCE OF ELASTIC TUBE

BACKGROUND OF THE INVENTION

1. Field of the Invention

The invention relates to a non-invasive method and device of measuring the pressure of fluid fluctuating in an elastic tube, particularly to a method and device of measuring the actual continuous pressure of fluid inside the elastic tube and the dynamic compliance of the elastic tube.

2. Description of the Related Art

The related techniques of the invention are the measurements of the instantaneous blood pressure in artery and the compliance of the blood vessel. The parameters of the blood pressure and arterial compliance are crucial for diagnosis of human health. The present developments are described as follows:

Methods to Measure the Arterial Blood Pressure

Since Marey (1876) first invented the sphygmograph to measure the blood pressure, many researchers have been trying to develop a non-invasive, convenient and reliable instrument to measure the blood pressure in an artery for medicine and health care. In the clinic, blood pressure is measured almost exclusively using non-invasive intermittent techniques, of which the auscultatory and the computerized oscillometric method are most often used. However, both methods only provide a momentary value for systolic blood pressure (SBP), diastolic blood pressure (DBP) and mean blood pressure (MBP).

Conversely, there are three methods to non-invasively detect the instantaneous arterial blood pressure: arterial tonometry based on the coplanar measurement (Pressman and Newgard 1963, Mackay 1964), Penń az's method (Penń az 1973, Wesseling 1984, Wesseling and Penń az 1986) and the volume-compensation method (Yamakoshi et al 1979, 1980). The latter two are based on the vascular unloading technique (Geddes 1970, Shirer 1962, O'Brien and O'Malley 1991).

Radial artery tonometry such as HDI CvProfilor (Cohn et al 1995), SphygmoCor (Giot and Dcgautc 1996), Pulsepen (Sale et al 2004) and Colin CBM-7000 arterial tonometry (manufactured by the Colin Corporation, Japan) employs the principle of applanation tonometry, where the artery is partially compressed against a hard structure to provide a continuous read-out of the pulse pressure waveform without the use of an occluding cuff. However, in order to calibrate the pressure measurement, the SBP, DBP and MBP in the opposite arm must also be measured by the auscultatory or cuff-oscillometric method for proportionally estimating the intra-arterial blood pressure. Thus two devices must be used at the same time to measure the blood pressures, which is a major drawback for its medical applications. Besides, the transmission characteristics of the blood pressure from the artery to the skin are not linear or constant.

Finapres (Boehmer 1987) or Portpres is a non-invasive continuous finger arterial blood pressure monitor based on the vascular unloading technique. With the volume-clamp method of Penń az, the finger arteries are clamped at a fixed diameter by applying an external pulsating pressure via an inflatable bladder mounted in a finger cuff and a fast-acting servo system. Finapres uses the criteria of Wesseling for determination of the setpoint. The diameter at which the finger arteries are clamped is determined from an infrared plethysmograph mounted in the finger cuff, such that the transmural pressure is zero and the cuff pressure is then equal to the intra-arterial pressure by assuming the ideal transmission of the pulsating pressure from the artery to the cuff. Later, Yamakoshi et al proposed the volume-compensation method to improve the servo reference, and developed a local pressurization technique to design a pad-type cuff sphygmomanometer (Tanaka et al 2005) for finger and wrist to avoid the occluding cuff encircling the biological segment that makes it uncomfortable in long-term measurements.

In summary, none of the above methods measures the actual instantaneous blood pressure in an artery, mainly because these methods are not capable of determining the transmission characteristics of the tissue and blood vessel. A possible approach to obtain these characteristics is to decouple the pulsation of the blood vessel from the tissues by using control and identification techniques.

Methods to Detect the Arterial Compliance

The cardiovascular diseases are mainly caused from arterial angiosclerosis. The estimation of the arterial angiosclerosis is primarily related the compliance of blood vessel. However, it is difficult to directly measure the compliance directly at present, because computing the compliance needs two signals of pressure and the variation of vascular volume (or diameter) simultaneously, and it is not easy to place two sensors to acquire signals at same measuring point. Hence, the present non-invasive techniques to detect the degree of arterial angiosclerosis mainly involve measuring arterial blood pressure, ABI (Ankle Branch Index), PWV (Pulse Wave Velocity) and AEI (Artery Elasticity Index).

The most common diagnosis for hypertension disorder is the measurement of systolic blood pressure (SBP) and diastolic blood pressure (DBP) of arterial blood pressure; ABI (Ankle-Brachial Index) is typically used for assessing the vascular obstruction at lower extremities and suitable for detecting the vascular obstruction caused by thrombus (atherosclerosis); in case of PWV (Pulse Wave Velocity), based on the time reference provided by electrocardiogram (ECG), pulse pressure waveforms of arteries at two electrodes are captured respectively, and the arterial wave velocity for assessing the level of atherosclerosis can be measured via time difference between two pulse waves; and for AEI (Artery Elasticity Index), it uses the continuous blood pressure via modified Windkessel model to compute the Large Artery Elasticity Index (Capacitive Arterial Compliance) $C_1$ and the Small Artery Elasticity Index (Reflective Arterial Compliance) $C_2$. It is obvious that the abovementioned measuring techniques are based on continuous blood pressure, not directly detect the arterial compliance. Besides, in order to accurate measuring the compliance of blood vessel, not only to have pressure and variation of vascular volume (or diameter) signals, but also the pulsation of blood vessel should not be affected by surrounding tissue.

In 2007, the present inventor developed an innovative blood pressure measurement technique, named TCM (Tissue Control Method), which by maintaining the DC part of blood pressure and tracking the AC part of blood pressure to cause the vascular truly unloading; the blood vessel is pulsated without the effect of surrounding tissue. Accordingly, the variation of vascular diameter is obtained, but meanwhile, the AC part of blood pressure is lost, that is the reference pressure for controller is absent as well. For estimating vascular impedance, the self-adaptive control algorithm is adopted, and the peak-to-peak blood pressure of the previous pulse is taken as reference pressure, by which, the beat-based intra-vascular continuous blood pressure could be obtained, but obviously the value is inaccurate, as shown in FIG. 11; in addition, the obtained arterial vascular impedance is just an approximate mean value in one pulse pressure cycle, as shown in FIG. 10. In other words, although TCM method could lead to the unloading state of the blood vessel, the absence of reference pressure causes the actual continuous blood pressure and the dynamic compliance of the blood vessel to be unobtainable. The present inventor then proposes a real-time based decoupling technique, named VLDT (Vascular Unloading Decoupling Technique), to measure the actual continuous pressure of fluid in the elastic tube and the dynamic compliance of elastic tube as well.

SUMMARY OF THE INVENTION

The present invention is based upon the Vascular Unloading Decoupling Technique (VLDT) to measure the actual continuous pressure of fluid $P_b$ inside the elastic tube and the dynamic compliance of elastic tube $C_v$ in real-time based.

The principle of the real-time based VLDT is primarily separated the continuous pressure of fluid $P_b$ into two parts, DC part of fluid pressure $\overline{P}_b$, and AC part of fluid pressure $\Delta P_b$. Then control the displacement of DC-driven actuator to maintain the DC part of fluid pressure $\overline{P}_b$ to be the same as the DC part of sensor's pressure $\overline{P}_s$, i.e. $\overline{P}_s = \overline{P}_b$. The pressure sensor is placed on the top of the tissue which is surrounding the elastic tube. This special location is named as critical depth $\overline{\lambda}_s$. At critical depth $\overline{\lambda}_s$, the measured impedance $\overline{Z}_s = \overline{P}_s/\overline{\lambda}_s$ is the impedance of the surrounding tissue $\overline{Z}_t$ only without the impedance of elastic tube involved, i.e. $\overline{Z}_s = \overline{Z}_t = K_t$. It says that the surrounding tissue is decoupled from elastic tube. In the mean time, move the AC-driven actuator to tracking the AC part of fluid pressure $\Delta P_b$ to maintain the pressure sensor only have the DC part of fluid pressure $\overline{P}_b$ without AC part of fluid pressure $\Delta P_b$, $P_s = \overline{P}_b$. Then the surrounding tissue will act as the rigid body while the elastic tube is pulsating itself without the effect of the surrounding tissue, that is the impedance of surrounding tissue is unchanged, $Z_t = K_t$; the displacement of AC-driven actuator $\Delta \lambda_s$, is then equal to the variation of elastic tube diameter $\Delta \lambda_v$, i.e. $\Delta \lambda_s = \Delta \lambda_v$. Then the pulsation of elastic tube is decoupled from surrounding tissue as well. This is the key point that we may identify the impedance of elastic tube $Z_v$ under decoupling condition, and in turns to compute the AC part of fluid pressure by $\Delta P_b = -\Delta \lambda_s Z_v$.

However, after tracking the AC part of fluid pressure $\Delta P_b$ completely, the pressure sensor can only have DC part of fluid pressure $\overline{P}_b$ without any AC part of fluid pressure $\Delta P_b$, i.e. $P_s = \overline{P}_s + \Delta P_s = \overline{P}_b$; $\Delta P_s = 0$. Although the variation of the elastic tube diameter is obtained, i.e. $\Delta \lambda_s = \Delta \lambda_v$, but without AC part of fluid pressure $\Delta P_b$, it cannot compute the impedance of elastic tube $Z_v$. To remedy this problem, the present inventor employs the self-adaptive control algorithm which confines the error of AC part of sensor's pressure $\Delta P_e$ within the acceptable level by setting the open control loop gain equals to a constant $K_a$. The open loop gain is the product of AC control gain $G_a$ and the parallel impedance $H_1$, i.e. $G_a H_1 = K_a$. For example, if let $K_a = 199$, it will limit the error of AC part of fluid pressure $\Delta P_b$ within $1/(1+K_a) = 0.5\%$ of range. Thus, the parallel impedance $H_1$ will be calculated by $K_a$ times of error of AC part of sensor's pressure divided by the displacement of AC-driven actuator as shown in FIG. 6, i.e. $H_1 = \Delta \hat{P}_b / \Delta \lambda_s = -K_a \Delta P_e / \Delta \lambda_s$, where the parallel impedance $H_1$ is the equilibrium impedance of the impedance of surrounding tissue $Z_t = K_t$ and impedance of elastic tube $Z_v$ in parallel, i.e. $H_1^{-1} = Z_t^{-1} + Z_v^{-1}$. Through the given impedance of surrounding tissue $Z_t$, the impedance of elastic tube $Z_v$ can then be computed in case that the parallel impedance $H_1$ is obtained, i.e. $Z_v^{-1} = H_1^{-1} - Z_t^{-1}$. In other word, by adjusting the AC control gain $G_a$ to have a constant open loop gain $K_a$, it can compute the impedance of elastic tube $Z_v$ and the actual continuous pressure of fluid $P_b$, provided that the error of AC part of sensor's pressure $\Delta P_b$ is given.

According to the control theory and FIG. 6, the error of AC part of sensor's pressure $\Delta P_s = -\Delta P_e$ is related to the reference pressure $\Delta \hat{P}_b$ as $\Delta P_s = -\Delta \hat{P}_b / (1+K_a)$. In order to have the precise error of AC part of sensor's pressure $\Delta P_s$, obtaining the instant reference pressure $\Delta \hat{P}_b$ is crucial. However, FIG. 6 shows that the AC part of sensor's pressure is the sum of reference pressure $\Delta \hat{P}_b$ and output pressure $\Delta \tilde{P}_b$ of parallel impedance $H_1$, i.e. $\Delta P_s = \Delta \hat{P}_b + \Delta \tilde{P}_b$. It indicates that the pressure sensor is unable to detect the instant reference pressure $\Delta \hat{P}_b$ at normal control period. The present inventor proposed the Step-Hold control algorithm to estimate the reference pressure at Hold stage and tracking the AC part of fluid pressure $\Delta P_b$ at Step stage by turns. At Hold stage (n−1 stage), by stopping the movement of AC-driven actuator, $\Delta \lambda_s(n-1) = 0$, will cause output pressure of parallel impedance is equal to zero, $\Delta \tilde{P}_b(n-1) = 0$, and the AC part of pressure sensor then directly sense the reference pressure signal $\Delta \hat{P}_b(n-1)$ only, i.e. $\Delta P_s(n-1) = \Delta \hat{P}_b(n-1)$. Use three Hold stages at beginning to have three instant reference pressures $\Delta \hat{P}_b(n-3)$、$\Delta \hat{P}_b(n-2)$、and $\Delta \hat{P}_b(n-1)$ and use the cubic spline curve fitting technique to estimate the n stage of reference pressure $\Delta \hat{P}_b(n)$, then compute the impedance of elastic tube $Z_v(n)$ and the AC control gain $G_a(n)$ at Hold stage. After that, then goes to the Step stage (n stage) to actuate the AC-driven actuator with AC control gain $G_a(n)$ that maintains the AC part of sensor's pressure is equal to the one of $(1+K_a)$th of reference pressure, i.e. $\Delta P_s(n) = -\Delta \hat{P}_b(n)/(1+K_a)$ and earn the variation of elastic tube diameter from AC part of displacement sensor, i.e. $\Delta \lambda_s(n) \cong \Delta \lambda_v(n)$. Hence the n stage of fluid pressure $P_b(n) = \overline{P}_s(n) - \Delta \lambda_s(n) Z_v(n)$ is attained. After completing the Step stage, return to Hold stage, and repeat the procedure until the measurement is finished. Therefore, VLDT is able to give the real-time continuous fluid pressure $P_b(n)$ and the dynamic impedance of elastic tube $Z_v(n)$ at the stage of n=1, 3, 5, ....

In summary, one of the objectives of the present invention is to provide a non-invasive method and device of measuring the real-time continuous pressure of fluid inside the elastic tube and the dynamic compliance of the elastic tube for solving the abovementioned problems. By using the Vascular Loading Decoupling Technique (VLDT) to decouple the pulsation of elastic tube from other surrounding tissues, thus the real-time continuous pressure of the fluid fluctuating in the elastic tube and the dynamic impedance of the elastic tube can be accurately measured.

In case of AC-driven actuator is not capable of fully tracking the AC part of fluid pressure $\Delta P_b$; the present inventor extends the VLDT decoupling theory into the area of partially decoupling of elastic tube. Under these circumstances, it can measure the real-time continuous pressure of fluid in elastic tube as well, but the partially decoupled dynamic impedance of elastic tube is obtained. The detailed descriptions are interpreted in the following related paragraphs.

Further, the dynamically equivalent mechanical characteristics, such as mass $M_v(n)$, damping $D_v(n)$ and stiffness $K_v(n)$, of the elastic tube can be extracted from the dynamic impedance of elastic tube $Z_v(n)$ by using identification technique, wherein the reciprocal of the stiffness $K_v(n)$ is the dynamic compliance of the elastic tube $C_v(n)$. It should mention that the obtained dynamic compliance of elastic tube is very meaningful, especially used for the measurement of compliance of blood vessel, because the measured compliance of blood vessel has two distinguished features: Firstly, the compliance of blood vessel is measured by the definition of compliance of blood vessel, i.e. $C_v(n) \equiv \Delta\lambda_v(n)/\Delta P_v(n)$, not estimated from the continuous blood pressure by Windkessel model; Secondary, it is measured under the situation of solely pulsation of blood vessel without the effect of other surrounding tissues. Thus the measured compliance is more validity of accuracy than other compliance measuring methods. Therefore, the second objective of the present invention is the measurement of dynamic compliance of elastic tube by using VLDT.

Methods Based Upon VLDT Theory

The abovementioned elastic tube is wrapped by surrounding tissues, and the fluctuating fluid flows in the elastic tube, wherein the actual continuous fluid pressure $P_b$ and the dynamic compliance of elastic tube $C_v$ are to be measured by a non-invasive method according to the theory of VLDT. The methods based upon VLDT theory are depicted as following steps:

Step 1: Searching Initial Critical Depth $\overline{\lambda}_s$

At beginning, using Oscillometric Method, press the detection head by DC-driven actuator on the surface of the surrounding tissues which is right above the elastic tube, record the fluid pressure and the displacement of DC-driven actuator until the AC part of fluid pressure $\Delta P_b$ is disappeared and then return back to the original depth. Thereafter, move the detection head to the position called initial critical depth $\overline{\lambda}_s$, where the magnitude of AC part of fluid pressure $\Delta P_b$ is maximum. It is also the depth that the DC part of fluid pressure to be the same as the DC part of sensor's pressure $\overline{P}_s$, i.e. $\overline{P}_s = \overline{P}_b$.

Step 2: Determining the Decoupled Ratio K

Hold at initial critical depth $\overline{\lambda}_s$ for few seconds to compute the DC part of fluid pressure $\overline{P}_b$ which is the same of the DC part of sensor's pressure, i.e. $\overline{P}_s = \overline{P}_b$; and to examine the difference of AC part of sensor's pressure $\Delta P_s(\Delta n)$ for each sampling period $T_s$, where the sampling period is set as 2 milli-seconds. If the maximum of the difference of AC part of sensor's pressure $\Delta P_s(\Delta n)_{max}$ is exceed of the fully tracking ability of AC-driven actuator for each sampling period $\Delta P_s(\Delta n)_{ref}$, then the partially decoupling of elastic tube is enabled and set the decoupled ratio as $K = \Delta P_s(\Delta n)_{ref}/\Delta P_s(\Delta n)_{max}$, where $0 < K < 1$. Then set the DC part of sensor's pressure is $\overline{P}_s' = \overline{P}_b + (1-K)\Delta P_b$ and AC part of sensor's pressure is $\Delta P_s' = K\Delta P_b$; If not exceed, decoupled ratio is then set as K=1, it means that the AC-driven actuator is able to fully tracking the AC part of fluid pressure $\Delta P_b$.

Step 3: Measuring the Impedance of Elastic Tube $Z_{V2}(n)$ and the Fluid Pressure $P_b(n)$ in the Elastic Tube The theory of VLDT is to maintain the DC part of sensor's pressure as $\overline{P}_s' = \overline{P}_b + (1-K)\Delta P_b$ and to track the AC part of sensor's pressure as $\Delta P_s' = K\Delta P_b = -\Delta P_e'$ simultaneously.

Thus, the DC controller employs the self-adaptive control rule to limit the error of DC part of fluid pressure $\overline{P}_b$ within the acceptable level by setting the DC open control loop gain equals to a constant $K_d$. The DC open loop gain is the product of DC control gain $G_d$ and the parallel impedance $H_1$, i.e. $G_d H_1 = K_d$. For example, the error of DC part of fluid pressure $\overline{P}_b$ is less than 0.2%, if the DC open loop gain is 499 which is based upon control theory. In other word, the purpose of DC controller is to maintain the press down location to the critical depth $\overline{\lambda}_s'$ (or $\overline{\lambda}_s$, if K=1), where is the location that the DC part of sensor' pressure is equal to the DC part of fluid pressure $\overline{P}_s' = \overline{P}_b + (1-K)\Delta P_b$. In the mean time, the impedance of the surrounding tissues is computed by $Z_t(n) = \overline{P}_s'/\overline{\lambda}_s'$.

Simultaneously, the AC controller initiates a series of estimation of reference pressure, identification of elastic tube's impedance, tracking the AC part of fluid pressure $\Delta P_b$, and computation of fluid during the Step and Hold cycles. The details of AC part of controlling procedure are depicted as follows:

Hold-Stage-1

Use cubic spline curve fitting technique to estimate the reference pressure $\Delta \hat{P}_b'(n)$ according to the previous data $\Delta \hat{P}_b'(n-3)$、$\Delta \hat{P}_b'(n-2)$、and $\Delta \hat{P}_b'(n-1)$ which are measured from the AC part of sensor's pressure at AC-driven actuator in idling situation (Hold-stage), i.e. $\Delta \overline{\lambda}_s' = 0$.

Hold-Stage-2

Identify the parallel impedance $H_1(n)$ and calculate the impedance of elastic tube $Z_{v2}(n)$ by.

$$H_1(n) = -\frac{-K_a \Delta P_s'(n)}{\Delta \lambda_s'(n-1)} = \frac{\Delta P_s'(n) - \Delta \hat{P}_b'(n)}{\Delta \lambda_s'(n-1)} = \frac{\Delta P_e'(n) - \Delta \hat{P}_b'(n)}{\Delta P_e'(n-1) G_a(n-1)}$$

and $$\frac{1}{Z_{v2}(n)} = \frac{1}{H_1(n)} - \frac{1}{Z_t(n)}$$

Hold-Stage-3

Calculate the AC control gain $G_a(n) = K_d/H_1(n)$, then enter the Step-stage.

Step-Stage-1

Actuate the AC actuator to tracking the AC part of fluid pressure $\Delta P_b$ with control gain $G_a(n)$ and measure the AC part of displacement $\Delta \lambda_s'(n)$.

Step-Stage-2

Compute the fluid pressure $P_b(n)$ by following formula:

$$P_b(n) = \overline{P}_b'(n) + \Delta P_b'(n) = \overline{P}_s'(n) - Z_{v2}(n)\Delta \lambda_s'(n)$$

Repeat the Hold and Step stages to obtain the impedance of elastic tube $Z_{v2}(n)$ and the fluid pressure $P_b(n)$ at each cycle until the end of the measurement.

Step 4: Extracting the Dynamic Compliance of Elastic Tube $C_v(n)$ from Dynamic Impedance of Elastic Tube $Z_{V2}(n)$ By using parameter identification technique, a series of dynamic impedance of elastic tube $Z_{v2}(n)$ can provide a series of equivalent mechanical properties such as mass $M_v(n)$, damping $D_v(n)$ and stiffness $K_v(n)$, where the reciprocal of stiffness is the compliance of elastic tube $C_v(n)$.

Device Based Upon VLDT Theory

To realize the theory of VLDT, the device of the present invention comprises:

a detection unit is arranged on the surfaces of the surrounding tissues, at least consisting of a DC-driven actuator, an AC-driven actuator, a DC displacement sensor, an AC displacement sensor and a pressure sensor, wherein the AC-driven actuator is positioned in the DC-driven actuator and can be moved up and down relative to the DC-driven actuator independently, and the pressure sensor is arranged on the end face of the AC-driven actuator and contacting with the surfaces of the surrounding tissues;

a control unit is used for analyzing and processing signals and electrically connected with two actuators, two displacement sensors and a pressure sensor; towing to control both of DC part and AC part of fluid pressures, the control unit contains DC controller and AC controller.

The DC-driven actuator executes a displacement action of pressing the detection unit down to the surface of the surrounding tissues according to the control gain $G_d$ from the DC controller to maintain the DC displacement at critical depth $\overline{\lambda}_s$ all the time, the displacement of the DC-driven actuator is measured by attached DC displacement sensor, and the control gain $G_d$ is processed by the DC controller;

The AC controller of the control unit generates a signals of AC control gain $G_a$ to drive the AC-driven actuator up and down in order to track the AC part of fluid pressure $\Delta P_b$, and the AC displacement sensor measures the change of the displacement of elastic tube $\Delta \lambda_s$.

The pressure sensor is used for measuring the pressure $P_s$ on the surfaces of the surrounding tissues. An analyzing algorithm in the control unit decouples the measured pressure $P_s$ into DC part of sensor's pressure $\overline{P}_s$ and AC part of sensor's pressure $\Delta P_s$ feedback to DC and AC controllers for controlling.

BRIEF DESCRIPTION OF THE DRAWINGS

FIG. 1 is a schematic chart of the measuring device of the present invention.

FIG. 2a is a schematic chart of physical models for the known measurement method (TCM).

FIG. 2b is a schematic diagram of the equivalent impedance model for FIG. 2a.

FIG. 3a is a schematic chart of physical models for the present method (VLDT).

FIG. 3b is a schematic diagram of the equivalent impedance model for FIG. 3a.

FIG. 3c is a schematic diagram of the mechanical circuit model for FIG. 3b.

FIG. 3d is a simplified mechanical circuit model for FIG. 3c.

FIG. 3e is a mechanical circuit model under Vascular Loading Decoupling Control.

FIG. 7b is the plot for describing the Step 3 of FIG. 7a.

FIG. 10 is a comparison chart of the real and estimated impedances of blood vessel for Tissue Control Method (TCM).

FIG. 11 is a comparison chart of the real and estimated arterial blood pressures for Tissue Control Method (TCM).

DETAILED DESCRIPTION OF THE PREFERRED EMBODIMENTS

Figure 2D:
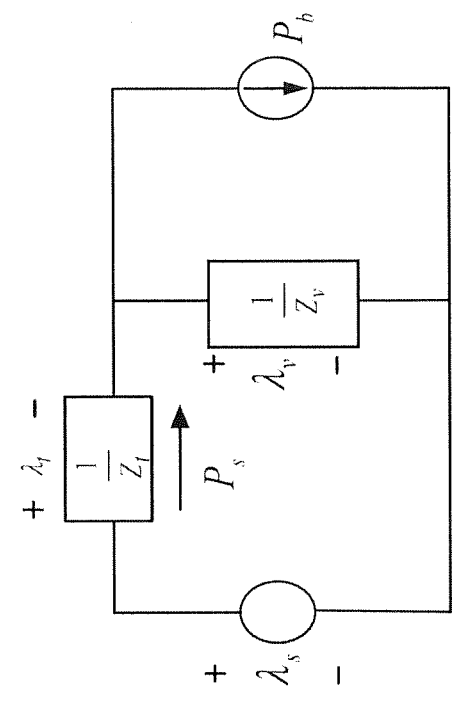
FIG. 2d is a simplified mechanical circuit model for FIG. 2c.

The present invention provides a non-invasive method and device to measure the real-time continuous pressure of fluid fluctuating in the elastic tube, where the elastic tube is surrounded by elastic tissues and the dynamic compliance of the elastic tube as well.

VLDT theory can be applied to a great variety of elastic tubes as long as the tube body has the elasticity and the fluctuating fluid flows in the tube body. In the embodiments of the present invention, the measurement of the real-time continuous pressure of the arterial blood pressure at wrist and the compliance of the blood vessel is the one of examples. The blood pressure in radial artery surrounded by muscle tissues and skin and the compliance of the radial artery are to be measured.

Key Technique of the Invention

Three key techniques of the present invention are described as follows:

I. Separating the Fluid Pressure into Two Parts and Using Control Techniques to Create the Decoupled Situation to Provide the Possibility of Measuring the Impedances of Surrounding Tissues and Elastic Tube Respectively It is quite impossible to measure the fluid pressure in elastic tube directly from the surface of surrounding tissues unless the impedances of surrounding tissues and the elastic tube are known for every measured point. It is also not easy to obtain both impedances of surrounding tissues and the elastic tube while they are moving simultaneously unless the movements of the surrounding tissues and the elastic tube are decoupled, i.e. the surrounding tissues move as a rigid body while the elastic tube is pulsating alone. Therefore, the first key technique of the present invention is to create the decoupled situation for surrounding tissues and elastic tube. The key is to divide the fluid pressure into DC part and AC part. Then a DC controller controls the movement of DC-driven actuator to maintain the DC part of sensor's pressure is equal to the DC part of Fluid pressure $\overline{P}_b$; i.e. the position of critical depth. At critical depth, the impedance of the surrounding tissues can be computed by DC part of sensor's pressure and DC part of displacement. Meanwhile, an AC controller drives the AC-driven actuator to fully track AC part of fluid pressure $\Delta P_b$ which causes the AC part of sensor's pressure is zero. Under these circumstances, the movement of surrounding tissues will act as the rigid body, i.e. the impedance of surrounding tissues is unchanged, whiles the elastic tube pulsating itself. It means the movement of surrounding tissues and the elastic tube are decoupled. Then the variation of the elastic tube diameter can be obtained from AC part of displacement on the surface, but the AC part of fluid pressure $\Delta P_b$ is lose due to the control theory.

II. Using Self-Adaptive and Step-Hold Control Algorithms to Estimate Reference Pressure, Identify the Impedance of Elastic Tube, Track the AC Part of Fluid Pressure and Finally Compute the Real-Time Fluid Pressure In order to remedy this problem, the AC part of fluid pressure $\Delta P_b$, will not be fully tracked; a limit of AC part of sensor's pressure within acceptable level is set Considering the nonlinear impedances of surrounding tissues and elastic tube, the self-adaptive control rule is used, then the AC open loop gain is set as a constant to ensure the limit of AC part of sensor's within the acceptable level, and the impedance of elastic tube can be calculated from the limit of AC part of sensor's pressure, AC open loop gain and the AC part of displacement. However, the limit of AC part of sensor's pressure is determined by the reference pressure. From FIG. 6, the sum of the reference pressure and the output of parallel impedance are equal to the limit of AC part of sensor's pressure. If the movement of the AC-driven actuator is hold, then the AC part of sensor's pressure will be the same as reference pressure; Thus a Step-Hold control rule as described in the theory of VLDT is adapted to make the measurement of the real time fluid pressure and the impedance of elastic tube to be feasible.

III. Extracting the Dynamic Compliance of Elastic Tube without the Effect of Surrounding Tissues from the Impedance of Elastic Tube by Using Parameter Estimation Technique The impedances of elastic tube contain the dynamic equivalent mass, damping and stiffness that can be further extracted by using parameter identification technique, wherein the reciprocal of the stiffness is the dynamic compliance of the elastic tube, which is the third key technique of this invention. One of the important applications, such as the measurement of the compliance of radial artery is creative and crucial in the diagnosis of angiosclerosis.

Measuring Device

The measuring device applied to the embodiment of the present invention is shown in the FIG. 1 and FIG. 3a and comprises a detection head 1 and a control unit (which is not shown in the figures), and the detection head 1 is arranged on the surfaces of tissues (the surface of the skin) and comprises a DC-driven actuator 10, an AC-driven actuator 11, a DC part of displacement sensor 12, an AC part of displacement sensor 13 and a pressure sensor 14 in the embodiments of the present invention, wherein the AC-driven actuator 11 is connected with the DC-driven actuator 10 and can independently move up and down relative to the DC-driven actuator 10, the pressure sensor 14 is positioned on the end face of the AC-driven actuator 11 and contacts with the surfaces of the surrounding tissues, the control unit is used for analyzing and processing signals, and the control unit is respectively connected with the DC-driven actuator 10, the AC-driven actuator 11, the DC part of displacement sensor 12, the AC part of displacement sensor 13 and the pressure sensor 14 electrically.

Physical Model for Known Measurement Method (Tissue Control Method, TCM)

FIG. 2a describes the physical model of the arterial blood pressure at the femur. The point at detection head 1 is labeled n, the skin surface is labeled a, the surface of the femur is d and the points b and c are the blood vessel's upper and lower points respectively. Assuming that the motion model of the arterial blood pressure is lumped, one may express each part, from the detection head 1 to the femur, by a mass element M, a damping element D and a stiffness element K to describe the motion behavior caused by arterial blood pressure transmitted from inside the vessel to the skin above. If the force transmissibility is equivalent to the pressure transmissibility from the blood vessel to the skin, the elements of M, D and K may be defined as $$M = \frac{P_M}{\lambda}, D = \frac{P_D}{\lambda}, K = \frac{P_K}{\lambda} \quad (1)$$

where P is the pressure and λ is the displacement. Then, by using the Laplace transform, one may define the impedance Z for each part as $$Z(s) = \frac{P}{\lambda} = Ms^2 + Ds + K \quad (2)$$

If the subscripts h, t1, v and t2 denote the parts of detection head 1, upper tissue, blood vessel and lower tissue, respectively, then the symbols of $Z_h$, $Z_{t1}$, $Z_v$ and $Z_{t2}$ indicate the impedances for the corresponding parts of the lumped model.

If the displacement λ is analogous to the voltage and the pressure P is analogous to the current, then the mechanical impedance will be analogous to the electrical admittance.

Figure 2C:
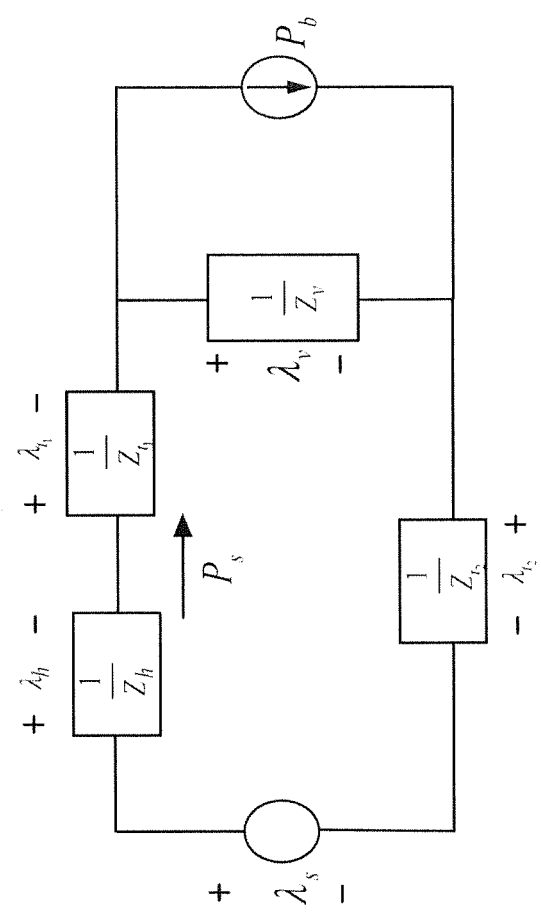
FIG. 2c is a schematic diagram of the mechanical circuit model for FIG. 2b.

FIG. 2c shows the equivalent mechanical circuit model for the transmission of arterial blood pressure at the femur. One may further combine the impedances of the detection head 1 $Z_h$, upper tissue $Z_{t1}$ and the lower tissue $Z_{t2}$ as the impedance of tissue $Z_t$ to simplify the circuit, as shown in FIG. 2d.

However, it should be noted that the experimental data show that the impedances are not constants as they vary with the pressed depth.

$$\frac{1}{Z_t} = \frac{1}{Z_h} + \frac{1}{Z_{t1}} + \frac{1}{Z_{t2}}$$

The abovementioned detection head 1 can be a cuff or an artery tonometry with actuators and sensors. If the artery tonometry is adopted as the detection head 1, the impedance of the detection head 1 is negligible compared with the tissues; however, if the cuff is adopted, the impedance of the detection head 1 should be taken into consideration.

Based upon the circuit theory, one may express the response of the blood pressure measured on the skin $P_s$ due to excitations of the pressed-down depth $\lambda_s$ and the arterial blood pressure $P_b$ as $$P_s = \frac{Z_t Z_v}{Z_t + Z_v} \lambda_s + \frac{Z_t}{Z_t + Z_v} P_b$$

Physical Model for Vascular Loading Decoupling Technique (VLDT)

In case of AC-driven actuator 11 is not capable of fully tracking the AC part of fluid pressure $\Delta P_b$; the present inventor extends the decoupling theory into the area of partially decoupling of elastic tube. The physical model is re-constructed as shown in FIG. 3a.

The difference between FIG. 3a and FIG. 2a is that FIG. 3a separates the arterial blood vessel into two parts: interior of blood vessel and exterior of blood vessel. The interior of blood vessel is the part of the AC part of blood pressure will be tracking and the exterior of blood vessel is the part of AC part of blood pressure and combined with DC part of blood pressure will be maintained. Therefore, the equivalent lumped circuit is depicted as FIG. 3c, where the impedances of detection head 1, upper tissue, exterior of blood vessel and lower tissue are in parallel and can be simplified as FIG. 3d. The equivalent impedance of surrounding tissues $Z_t$ is expressed as follows:

$$\frac{1}{Z_t} = \frac{1}{Z_h} + \frac{1}{Z_{t1}} + \frac{1}{Z_{v1}} + \frac{1}{Z_{v2}} + \frac{1}{Z_{t2}} \quad (3)$$

And the response of the blood pressure measured on the skin $P_s$ due to excitations of the pressed-down depth $\lambda_s$ and the arterial blood pressure $P_b$ as $$P_s = \frac{Z_t Z_{v2}}{Z_t + Z_{v2}} \lambda_s + \frac{Z_t}{Z_t + Z_{v2}} P_b \quad (4)$$

where the arterial blood pressure $P_b$ can be summed by DC part of blood pressure $\overline{P}_b$, and the AC part of blood pressure $\Delta P_b$.

Determination of Decoupled Ratio K for Limiting Dilatable Range of Arterial Blood Vessel During Pulsation For each measured point, if the maximum of the difference of AC part of sensor's pressure $\Delta P_s(\Delta n)_{max}$ is exceed of the fully tracking ability of AC-driven actuator 11 for each sampling period $\Delta P_s(\Delta n)_{ref}$, then the partially decoupling of elastic tube is enabled and set the decoupled ratio as K=

$\Delta P_s(\Delta n)_{ref}/\Delta P_s(\Delta n)_{max}$, where $0<K<1$. Then set the DC part of sensor's pressure is $\overline{P}_s'=\overline{P}_b+(1-K)\Delta P_b$ and AC part of sensor's pressure is $\Delta P_s'=K\Delta P_b$. If not exceed, decoupled ratio is then set as K=1, it means that the AC-driven actuator 11 is able to fully tracking the AC part of fluid pressure $\Delta P_b$.

Analysis of DC Part of Blood Pressure Excitation $\overline{P}_b'$

If one presses the skin to a critical depth $\overline{\lambda}_s'$ such that the DC part of sensor's pressure $\overline{P}_s'$ measured on the skin equals the DC part of arterial blood pressure $\overline{P}_b'$, then equation (4) can be written as $$\overline{P}_s' = \frac{\overline{Z}_t \overline{Z}_{v2}}{\overline{Z}_t + \overline{Z}_{v2}}\overline{\lambda}_s + \frac{\overline{Z}_t}{\overline{Z}_t + \overline{Z}_{v2}}\overline{P}_b', \quad (5)$$
$$\overline{P}_s' = \overline{P}_b'$$

Solving equation (5) gives $$\overline{P}_s' = \overline{Z}_t \overline{\lambda}_s' = \overline{P}_b' \Rightarrow \overline{Z}_s = \frac{\overline{P}_s'}{\overline{\lambda}_s'} = \overline{Z}_t \quad (6)$$

Obviously, equation (6) states that at the critical depth $\overline{\lambda}_s'$ where, the impedance measured on the skin is equal to the equivalent impedance of detection head 1, upper tissue, exterior of blood vessel and lower tissue only, and the interior of blood vessel is no longer involved in the analysis. It further illustrates that the impedance of the interior of arterial blood vessel, $\overline{Z}_{v2}$ and the impedance of other surrounding tissues, $\overline{Z}_t$ are decoupled.

Analysis of AC Part of Blood Pressure Excitation $\Delta\overline{P}_b'$

When the AC part of arterial blood pressure $\Delta\overline{P}_b'$ is imposed on the DC part of the arterial blood pressure $\overline{P}_b'$ at the critical depth $\overline{\lambda}_s'$, equation (4) can be rewritten as $$\overline{P}_s' + \Delta P_s' = \frac{Z_t Z_{v2}}{Z_t + Z_{v2}}(\overline{\lambda}_s' + \Delta\lambda_s') + \frac{Z_t}{Z_t + Z_{v2}}(\overline{P}_b' + \Delta P_b') \quad (7)$$

Substituting the equation (6) and $\overline{P}_s'=\overline{P}_b'=\overline{Z}_t\overline{\lambda}_s'$ into the equation (7) yields $$\Delta P_s' = \frac{Z_t Z_{v2}}{Z_t + Z_{v2}}\left(1 - \frac{\overline{Z}_t}{\overline{Z}_t}\right)\overline{\lambda}_s' + \frac{Z_t Z_{v2}}{Z_t + Z_{v2}}\Delta\lambda_s' + \frac{Z_t}{Z_t + Z_{v2}}\Delta P_b' \quad (8)$$

If one moves the critical depth $\overline{\lambda}_s'$ up and down to keep the AC part of the sensor's pressure measured on the skin $\Delta P_s'$ equal to zero and maintain the impedance of the tissue $Z_t=\overline{Z}_t$, then equation (8) becomes $$\Delta\lambda_s' = -\frac{1}{Z_{v2}}\Delta P_b' = \Delta\lambda_v' \quad (9)$$

where $\Delta\lambda_v'$ is the variation of the interior of blood vessel diameter. It also represents the displacement varying from the location of the zero transmural pressure of the interior of blood vessel. This derivation reveals that the variation of the displacement measured on the skin is equivalent to the variation of the interior of blood vessel diameter due to the AC part of the arterial blood pressure. The significant implication of this result is that the pulsation of the interior of blood vessel is therefore decoupled from the surrounding tissues, enabling one to identify the impedance of interior of blood vessel and to estimate the intra-arterial blood pressure as shown equation (10) in turn.

$$P_b = \overline{P}_b' + \Delta P_b' = \overline{P}_s' - Z_{v2}\Delta\lambda_s' \quad (10)$$

For obtaining the situation of (10), we present the LVDT to detect the variation of blood vessel diameter and the real time intra-arterial blood pressure.

Vascular Loading Decoupling Technique (VLDT)

Figure 4:
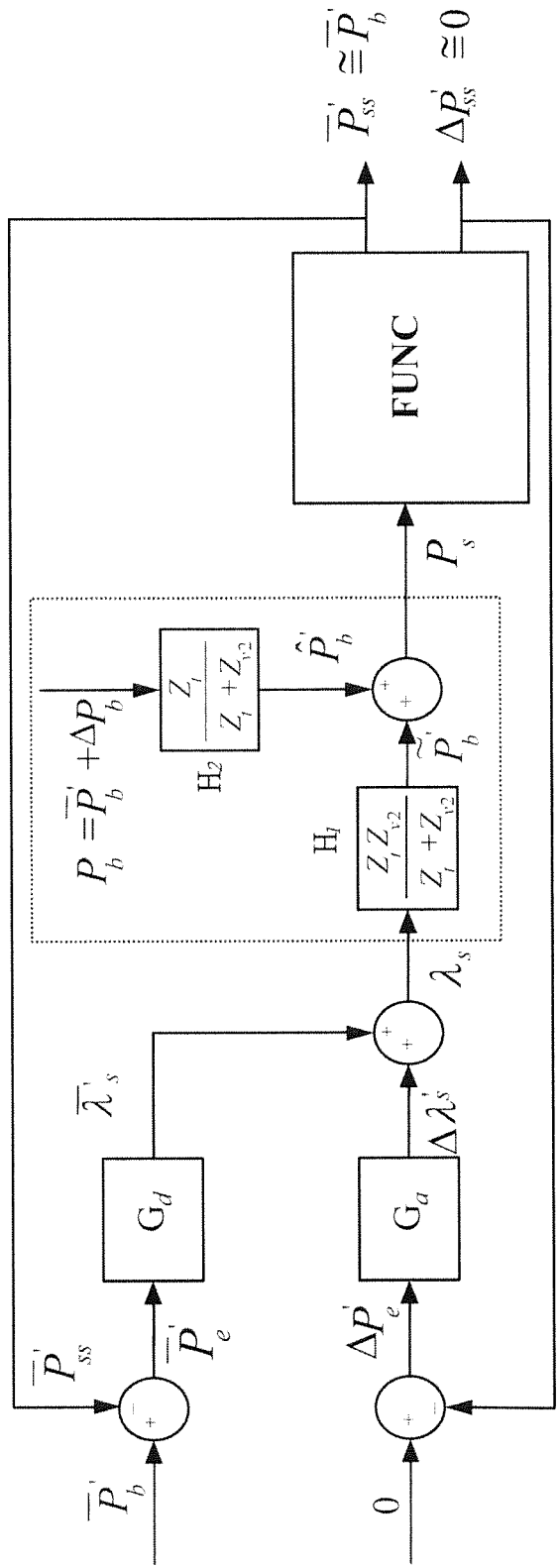
FIG. 4 is a control block diagram for VLDT which comprises of DC control block and AC control block. The whole control is to track the AC part of arterial blood pressure at critical depth.

The key for the VLDT is to track the AC part of arterial blood pressure at critical depth by allowing the blood vessel to pulsate with constant impedance of surrounding tissues. Based upon equations (7) and (8), a control diagram for VLDT is drawn in FIG. 4, where $G_d$ is the block diagram of DC controller and DC-driven actuator 10 and $G_a$ is the AC controller and the AC-driven actuator 11 respectively. Two displacement sensors, DC part of displacement sensor 12 and AC part of displacement sensor 13 are attached with DC-driven actuator 10 and AC-driven actuator 11 and sensing their movements $\overline{\lambda}_s'$ and $\overline{\Delta\lambda}_v'$ respectively. Whereas, the pressure $P_s$ measured by the pressure sensor 14 is processed by a FUNC program to obtain a DC part of sensor's pressure $\overline{P}_{ss}'$ and an AC part of sensor's pressure $\Delta P_{ss}'$, which are taken as feedback signals for DC controller and AC controller, respectively.

System Response Due to DC Part of Arterial Blood Pressure $\overline{P}_b'$

Figure 5:
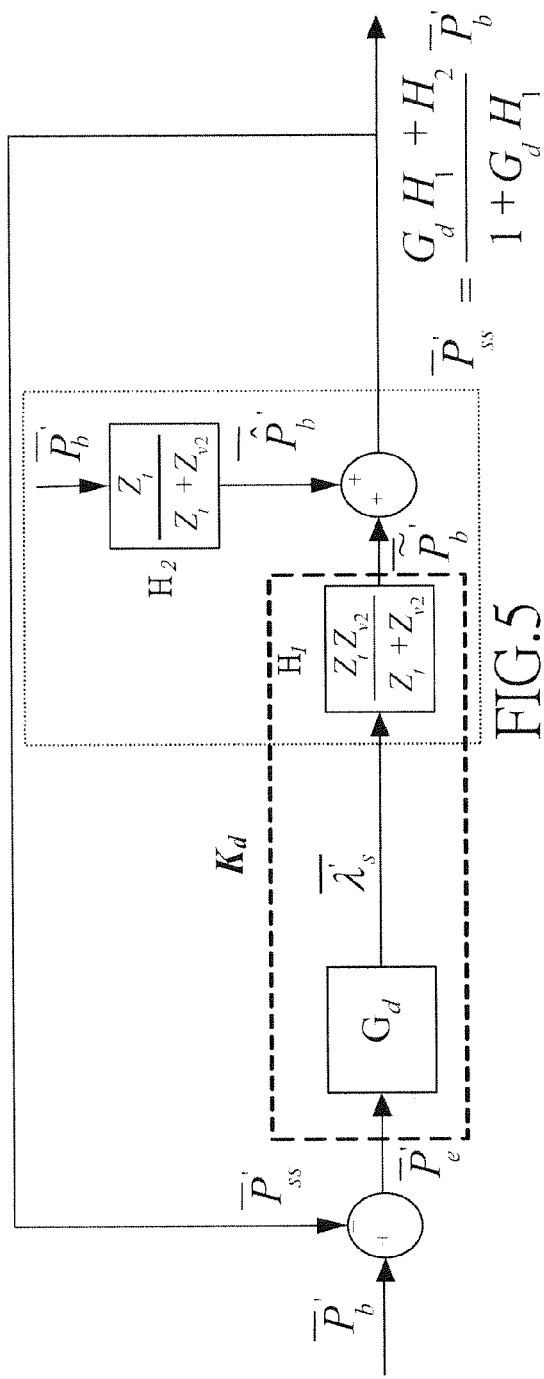
FIG. 5 is a DC control block diagram of maintaining the DC part of arterial blood pressure at critical depth.

FIG. 5 is block diagram for DC control of VLDT. The purpose of DC control is to maintain the detection head 1 at critical depth $\overline{\lambda}_s'$ where the DC part of sensor's pressure is equal to the DC part of arterial blood pressure, $\overline{P}_s'=\overline{P}_b'$. In order to limit the measuring error of DC part of arterial blood pressure and the nonlinear of impedances of surrounding and blood vessel, the present invention proposes the self-adaptive control rule to set the DC open loop gain $K_d$, as constant, where $K_d=G_dH_1$. Based upon the DC part of arterial blood pressure is $\overline{P}_s'=\overline{P}_b+K\Delta P_b=\overline{P}_b'$ and control theory, the error of the DC part of arterial blood pressure $e_d$ can be expressed as equation (11).

$$e_d = \frac{1-H_2}{1+G_dH_1}\overline{P}_b' \quad (11)$$

where the impedance $H_2=Z_t/(Z_t+Z_{v2})$ is smaller than 1.

Therefore, set the DC open loop gain $K_d=G_dH_1=499$, the error of DC control results in equation (11) is less than 0.2%. It means that setting the DC control gain $G_d$ to have DC open loop gain $K_d$ is constant will keep the detection head 1 nearly to the critical depth, which is similar to the analysis of DC part of arterial blood pressure excitation.

Figure 6:
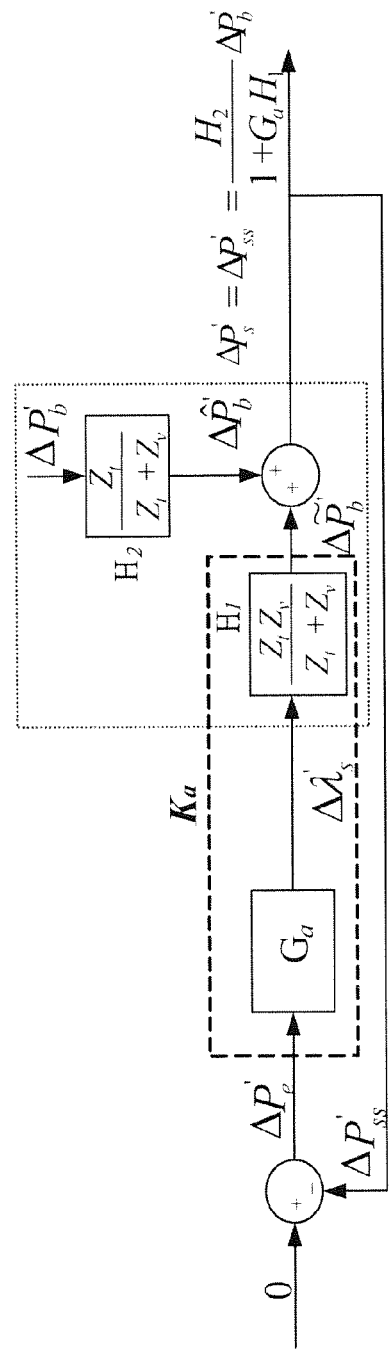
FIG. 6 is an AC control block diagram of tracking the AC part of arterial blood pressure at critical depth.

System Response Due to AC Part of Arterial Blood Pressure $\Delta\overline{P}_b'$ When the DC-driven actuator 10 is pressed to reach the critical depth $\overline{\lambda}_s'$, an AC controller is needed to move the AC-driven actuator 11 with displacement $\Delta\lambda_s'$ in order to have the AC part of arterial blood pressure be zero, $\Delta P_b'=K\Delta P_b=0$, as shown in FIG. 6.

The control theory gives the error of the AC part of arterial blood pressure $e_a$ shown in equation (12).

$$e_a = 0 - \Delta P'_{ss} = \frac{-H_2}{1 + G_a H_1} \Delta P'_b \qquad (12)$$

Similarly, the self-adaptive control rule is used. Adjust the AC control gain 0, so as to maintain the AC open loop gain to be the fixed value, $G_a H_1 = K_a$. If set $K_a = 199$, the error of the AC part of arterial blood pressure $e_a$ is smaller than 0.5%. By now, the pulsation of the interior of arterial blood vessel at critical depth is similar to the analysis of AC part of arterial blood pressure $\Delta P_b'$.

From FIG. 6, it learns that the parallel impedance $H_1$ can be measured by equation (13).

$$H_1 = \frac{\Delta \tilde{P}'_b}{\Delta \lambda'} = \frac{K_a \Delta P'_e}{\Delta \lambda'} = \frac{-K_a \Delta P'_{ss}}{\Delta \lambda'} \qquad (13)$$

However, the AC part of sensor's pressure is the sum of the reference pressure $\Delta \hat{P}_b'$ and the output pressure $\Delta \tilde{P}_b'$ of parallel impedance $H_1$, $\Delta P_{ss}' = \Delta \hat{P}_b' + \Delta \tilde{P}_b'$. It cannot be measured with two unknown pressures unless to keep one of the pressure to be zero. Therefore, the present invention provides a Step-Hold control rule to cope with this problem. At Hold stage, let AC-driven actuator 11 is idling, the AC part of displacement is zero and causes the output pressure $\Delta \tilde{P}_b'(n-1)$ of parallel impedance is zero too, then the measurement of AC part of sensor's pressure is equal to the reference pressure, $\Delta P_{ss}'(n-1) = \Delta \hat{P}_b'(n-1)$.

Use three Hold stages at beginning to have three instant reference pressures $\Delta \hat{P}_b(n-3)$、$\Delta \hat{P}_b(n-2)$、and $\Delta \hat{P}_b(n-1)$, and employ the cubic spline curve fitting technique to estimate the n stage of reference pressure $\Delta \hat{P}_b(n)$, then compute the impedance of elastic tube $Z_v(n)$ at Hold stage by equations (14) and (15).

$$H_1(n) = -\frac{-K_a \Delta P'_{ss}(n)}{\Delta \lambda'_s(n-1)} \qquad (14)$$

$$= \frac{\Delta P'_{ss}(n) - \Delta \hat{P}'_b(n)}{\Delta \lambda'_s(n-1)}$$

$$= \frac{-\Delta P'_e(n) - \Delta \hat{P}'_b(n)}{\Delta P'_e(n-1) G_a(n-1)}$$

$$\frac{1}{Z_{v2}(n)} = \frac{1}{H_1(n)} - \frac{1}{Z_t(n)} \qquad (15)$$

and the AC control gain $G_a(n)$ is obtained by equations (16) as well.

$$G_a(n) = \frac{K_a}{H_1(n)} \qquad (16)$$

After that, then goes to the Step stage (n stage) to actuate the AC-driven actuator 11 with AC control gain $G_a(n)$ that maintains the AC part of sensor's pressure is equal to the one of $(1+K_a)$th of reference pressure, i.e. $\Delta P_{ss}'(n) = -\Delta \hat{P}_b'(n)/(1+K_a)$ and earn variation of elastic tube diameter from AC part of displacement sensor 13, i.e. $\Delta \lambda_s'(n) \cong \Delta \lambda_v'(n)$.

Finally, compute the n stage of fluid pressure by equation (17).

$$P_b(n) = \overline{P}_s'(n) - \Delta \lambda_s'(n) Z_{v2}'(n) \qquad (17)$$

Repeat the Hold and Step stages to obtain the impedance of elastic tube $Z_{v2}(n)$ and the fluid pressure $P_b(n)$ at each cycle until to the end of the measurement.

Identification of Real-Time Mechanical Characteristics (Mv, Dv and Kv) and Dynamic Compliance C3 of Arterial Blood Vessel In the light of the definition of impedance $Z_{v2}$, the equivalent mechanical characteristics, such as mass $M_v$, damping $D_v$ and stiffness $K_v$ constitute equation (18) as follows:

$$-Z_{v2}(s)\Delta \lambda_s' = \Delta P_b' \Rightarrow -(M_v s^2 + D_v s + K_v)\Delta \lambda_s' = \Delta P_b' \qquad (18)$$

Matrix parameters of the mass $M_v$, the damping $D_v$ and the stiffness $K_v$ can be identified via equation (18) through bilinear transform, as shown in equation (19):

$$\begin{bmatrix} M \\ D \\ K \end{bmatrix} = \begin{bmatrix} \Delta \lambda_s'(n) & \Delta \lambda_s'(n-1) & \Delta \lambda_s'(n-2) \\ \Delta \lambda_s'(n-1) & \Delta \lambda_s'(n-2) & \Delta \lambda_s'(n-3) \\ \Delta \lambda_s'(n-2) & \Delta \lambda_s'(n-3) & \Delta \lambda_s'(n-4) \end{bmatrix}^{-1} \qquad (19)$$

$$\begin{bmatrix} Z_{v2}(n) + 2Z_{v2}(n-1) + Z_{v2}(n-2) \\ Z_{v2}(n-1) + 2Z_{v2}(n-2) + Z_{v2}(n-3) \\ Z_{v2}(n-2) + 2Z_{v2}(n-3) + Z_{v2}(n-4) \end{bmatrix}$$

The mass $M_v$, the damping $D_v$ and the stiffness $K_v$ of the arterial blood vessel can be further extracted by equation (20) as follows:

$$M_v = \frac{T^2}{16}(M - D + K);$$

$$D_v = \frac{T}{4}(M - K); \qquad (20)$$

$$K_v = \frac{1}{4}(M + D + K)$$

where T is the sampling period.

The reciprocal of the stiffness $K_v$ is the dynamic compliance of the arterial blood vessel, which is defined as $C_3$ in the present invention and different from the Artery Elasticity Indexes of $C_1$ and $C_2$ calculated via Windkessel Model based upon the continuous arterial blood pressure. More important, $C_3$ is measured under the pulsation of the arterial blood vessel without the influence of surrounding tissues.

The Embodiment of Measurement Method of the Invention

Figure 7A:
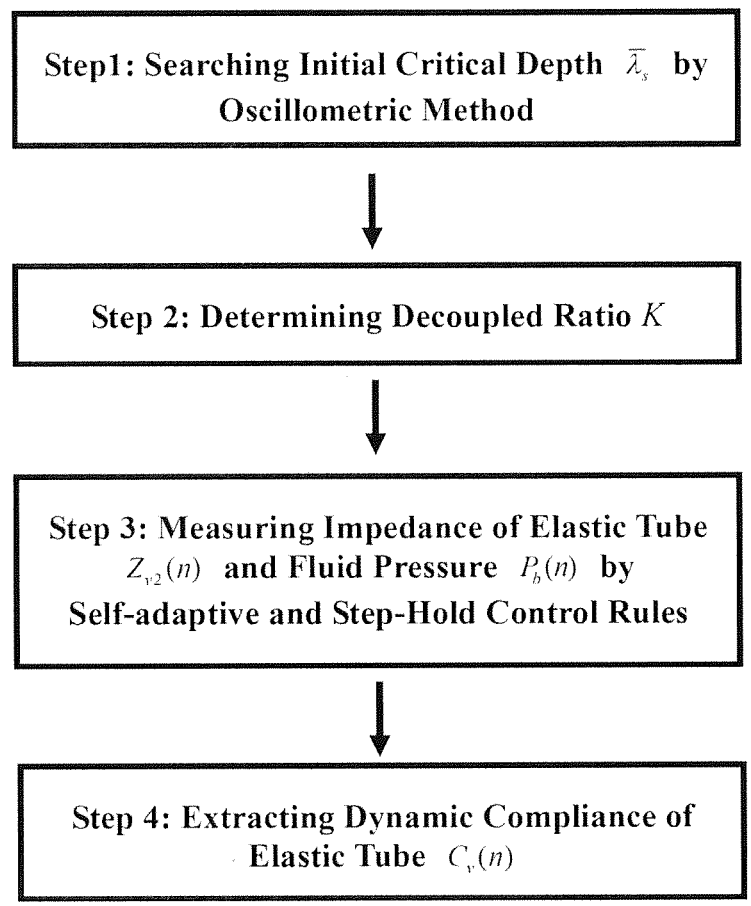
FIG. 7a is a measuring procedure for the embodiment of the present invention.
Figure 7B:
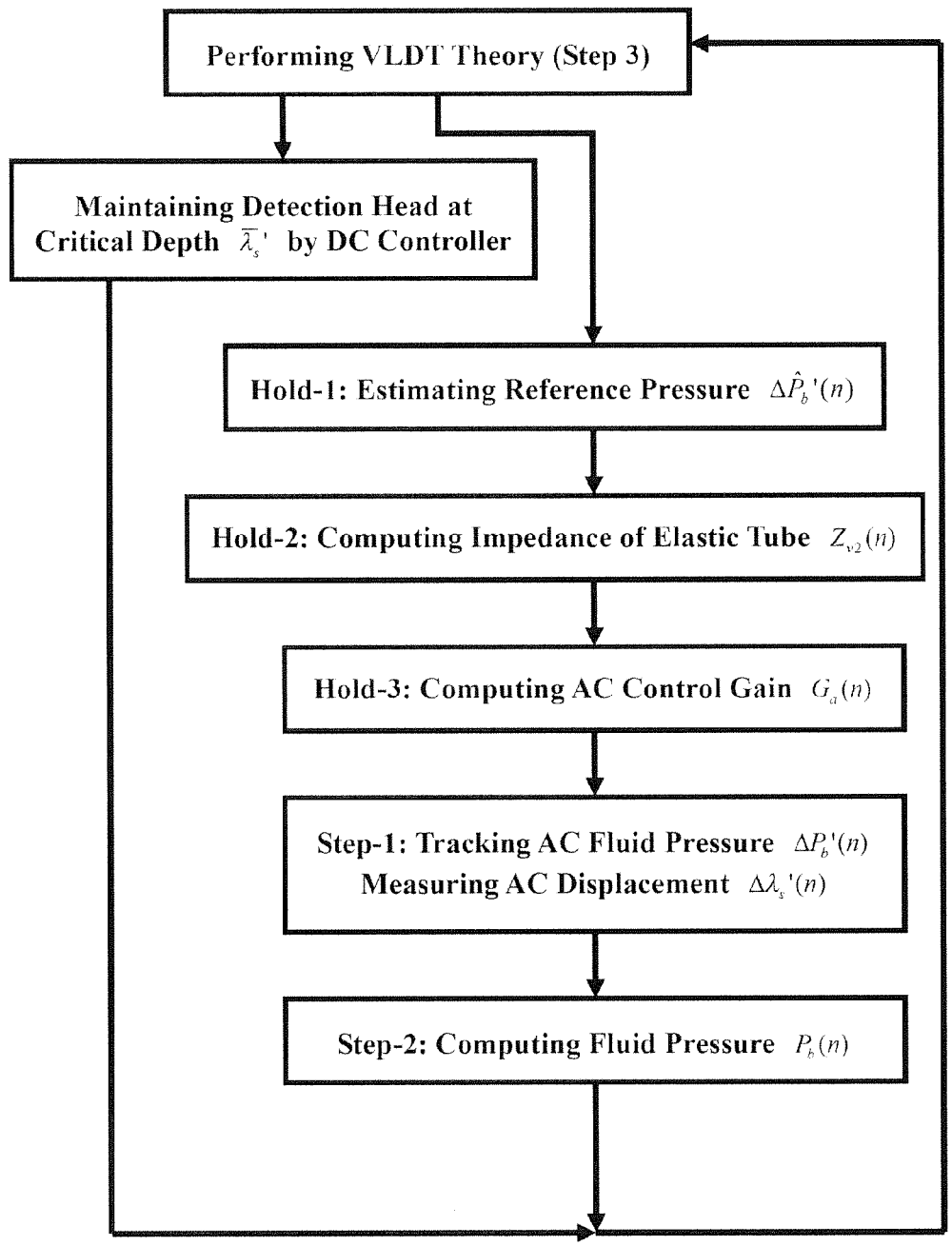

The embodiment of the present invention is shown in FIG. 7a and FIG. 7b, in which the full and the partial tracking AC part of arterial blood pressures are included. The degree of tracking of AC part of arterial blood pressure is determined by the decoupled ratio K defined by the capability of AC-driven actuator 11. The measurement of the embodiment mainly comprises the following steps:

Step 1: Searching an Initial Critical Depth $\overline{\lambda}_s$

At beginning, using Oscillometric Method, press the detection head 1 by DC-driven actuator 10 on the surface of the surrounding tissues to located the initial critical depth $\overline{\lambda}_s$, the DC-driven actuator 10 is right above the elastic tube, record the fluid pressure and the displacement of DC-driven actuator 10 until the AC part of fluid pressure $\Delta P_b$ is disappeared and then return back to the original depth. Thereafter, move the detection head 1 to the position called initial critical depth $\overline{\lambda}_s$, where the magnitude of AC part of fluid pressure $\Delta P_b$ is maximum. It is also the depth that the DC part of fluid pressure $\overline{P}_b$ to be the same as the DC part of sensor's pressure $\overline{P}_s$, i.e. $\overline{P}_s = \overline{P}_b$.

Step 2: Determining the Decoupled Ratio K

Hold at initial critical depth $\bar{\lambda}_s$, if, for few seconds to compute the DC part of fluid pressure $\bar{P}_b$ which is the same of the DC part of sensor's pressure $\bar{P}_s$, i.e. $\bar{P}_s=\bar{P}_b$; and to examine the difference of AC part of sensor's pressure $\Delta P_s(\Delta n)$ for each sampling period $T_s$ where the sampling period is set as 2 milli-seconds. If the maximum of the difference of AC part of sensor's pressure $\Delta P_s(\Delta n)_{max}$ is exceed of the fully tracking ability of AC-driven actuator 11 for each sampling period $\Delta P_s(\Delta n)_{ref}$, then the partially decoupling of elastic tube is enabled and set the decoupled ratio as $K=\Delta P_s(\Delta n)_{ref}/\Delta P_s(\Delta n)_{max}$, where 0<K<1. Then set the DC part of sensor's pressure is $\bar{P}_s'=\bar{P}_b+(1-K)\Delta P_b$ and AC part of sensor's pressure is $\Delta P_s'=K\Delta P_b$; If not exceed, then decoupled ratio is set as K=1, it means that the AC-driven actuator 11 is able to fully tracking the AC part of fluid pressure $\Delta P_b$.

Step 3: Measuring the Impedance of Elastic Tube $Z_{V2}(n)$ and the Fluid Pressure $P_b(n)$ in the Elastic Tube The theory of VLDT is to maintain the DC part of sensor's pressure as $\bar{P}_s'=\bar{P}_b+(1-K)\Delta P_b$ and to track the AC part of sensor's pressure as $\Delta P_s'=K\Delta P_b$ simultaneously.

Thus, the DC controller employs the self-adaptive control rule to limit the error of DC part of fluid pressure $\bar{P}_b$ within the acceptable level by setting the DC open control loop gain $K_d$ equals to a constant. The DC open loop gain is the product of DC control gain $G_d$ and the parallel impedance $H_1$, i.e. $G_d H_1 = K_d$. For example, the error of DC part of fluid pressure $\bar{P}_b$ is less than 0.2%, if the DC open loop gain is 499 which is based upon control theory. In other word, the purpose of DC controller is to maintain the press down location to the critical depth $\bar{\lambda}_s'$ (or $\bar{\lambda}_s$, if K=1), where is the location that the DC part of sensor' pressure is equal to the DC part of fluid pressure $\bar{P}_s'=\bar{P}_b+(1-K)\Delta P_b$. In the mean time, the impedance of the surrounding tissues is computed by $Z_t(n)=\bar{P}_s'/\bar{\lambda}_s'$.

Simultaneously, the AC controller initiates a series of estimation of reference pressure, identification of elastic tube's impedance, tracking the AC part of fluid pressure $\Delta P_b$ and computation of fluid during the Step and Hold cycles. The details of AC part of controlling procedure are depicted as follows:

Hold-Stage-1

Use cubic spline curve fitting technique to estimate the reference pressure $\Delta \hat{P}_b'(n)$ according to the previous data $\Delta \hat{P}_b'(n-3)$、$\Delta \hat{P}_b'(n-2)$、and $\Delta \hat{P}_b'(n-1)$ which are measured from the AC part of sensor's pressure at AC-driven actuator 11 in idling situation (Hold-stage), i.e. $\Delta \bar{\lambda}_s'=0$.

Hold-Stage-2

Identify the parallel impedance $H_1(n)$ and calculate the impedance of elastic tube $Z_{v2}(n)$ by.

$$H_1(n) = -\frac{-K_a \Delta P_s'(n)}{\Delta \lambda_s'(n-1)} = \frac{\Delta P_s'(n) - \Delta \hat{P}_b'(n)}{\Delta \lambda_s'(n-1)} = \frac{-\Delta P_e'(n) - \Delta \hat{P}_b'(n)}{\Delta P_e'(n-1) G_a(n-1)}$$

and $$\frac{1}{Z_{v2}(n)} = \frac{1}{H_1(n)} - \frac{1}{Z_t(n)}$$

Hold-Stage-3

Calculate the AC control gain $G_a(n)=K_a/H_1(n)$, then enter the Step-stage.

Step-Stage-1

Actuate the AC actuator to tracking the AC part of fluid pressure $\Delta P_b$ with control gain $G_a(n)$, and measure the AC part of displacement $\Delta \lambda_s'(n)$.

Step-Stage-2

Compute the real-time continuous fluid pressure $P_b(n)$ by following equation:

$$P_b(n)=\bar{P}_b'(n)+\Delta P_b'(n)=\bar{P}_s'(n)-Z_{v2}(n)\Delta \lambda_s'(n)$$

Repeat the Hold and Step stages to obtain the impedance of elastic tube $Z_{v2}(n)$ and the real-time continuous fluid pressure $P_b(n)$ at each cycle until the end of the measurement.

Step 4: Extracting the Dynamic Compliance of Elastic Tube $C_v(n)$ from Dynamic Impedance of Elastic Tube $Z_{V2}(n)$ By using parameter identification technique, a series of dynamic impedance of elastic tube $Z_{v2}(n)$ can provide a series of equivalent mechanical properties such as mass $M_v(n)$, damping $D_v(n)$ and stiffness $K_v(n)$, where the reciprocal of stiffness is the compliance of elastic tube $C_v(n)$.

Verification

Figure 8:
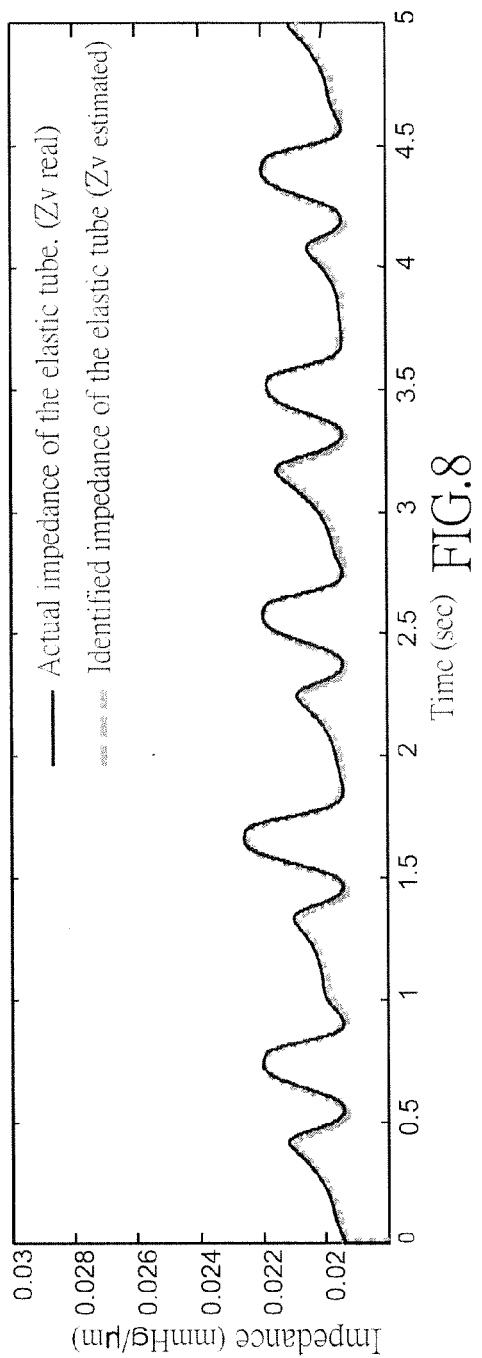
FIG. 8 is a comparison chart of the real and estimated impedances of blood vessel.
Figure 9:
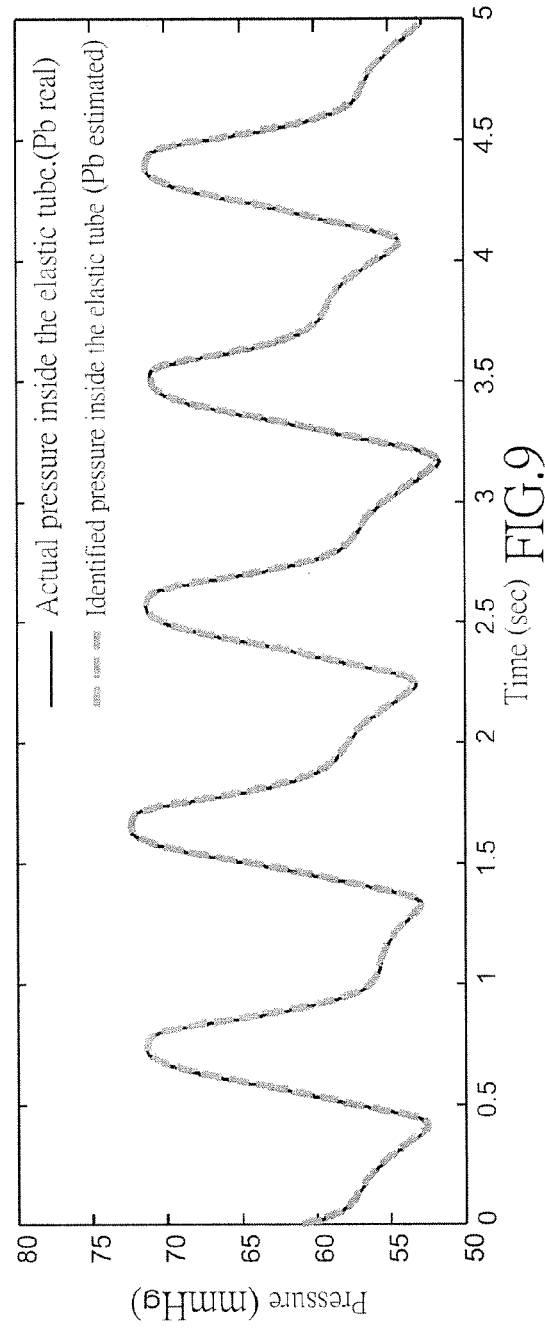
FIG. 9 is a comparison chart of the real and estimated arterial blood pressure.

In order to verify the feasibility of VLDT, nonlinear impedances of surrounding tissues and blood vessel and blood pressures based upon experiments are assumed. The simulation results run by MATLAB are shown in FIG. 8 and FIG. 9. FIG. 8 is a comparison chart of real and estimated of impedances of blood vessel; and FIG. 9 shows the comparison chart of real and estimated of arterial blood pressures. It all indicates that the results are satisfied and feasible in reality.

CONCLUSION

From the above, the measurement method and the measuring device provided by the invention are useful for measuring the real time fluid pressure in an elastic tube which surrounded by elastic tissues and the dynamic compliance of elastic tube as well. This invention can be extensively applied for detecting the degree of aging for elastic pipes after long run operations, or the some medical applications which need the real continuous blood pressure or dynamic compliance of blood vessel for more precisely diagnostic analyses.

What is claimed is:

1. A non-invasive method of measuring a real-time continuous pressure of fluid in an elastic tube and a dynamic compliance of the elastic tube, wherein elastic surrounding tissues are wrapped outside the elastic tube, and wherein a fluctuating fluid flows in the elastic tube, the fluid having a fluid pressure which can be divided into a DC part $\bar{P}_b$ and an AC part $\Delta P_b$, the method comprising:

using an oscillometric method, pressing a detection head by a DC-driven actuator on the surface of the surrounding tissues to locate an initial critical depth $\bar{\lambda}_s$;

holding at the initial critical depth to determine a decoupled ratio K for partial or full tracking of the AC part of fluid pressure $\Delta P_b$;

actuating a DC-driven actuator to maintain a DC part of a sensor's pressure $\bar{P}_s$ as equal to the DC part of the fluid pressure $\bar{P}_b$, and setting a resulting new depth as the location of an updated critical depth $\bar{\lambda}_s'$;

setting an AC-driven actuator, separate from the DC-driven actuator, in an idling (hold) stage to obtain three previous reference pressures $\Delta \hat{P}_b'(n-3)$, $\Delta \hat{P}_b'(n-2)$, and $\Delta \hat{P}_b'(n-1)$, and estimating a reference pressure $\Delta \hat{P}_b'(n)$ for an actuated (step) stage;

using a constant AC open loop gain $K_a$ and a self-adaptive control rule to estimate a parallel impedance $H_1$ and compute an impedance of the elastic tube $Z_{v2}(n)$;

using the constant AC open loop gain $K_a$ and the parallel impedance $H_1$ to calculate an AC control gain $G_a$ for a next step stage;

sending an AC control gain $K_a$ from AC controller, and moving the AC-driven actuator to track the AC part of the fluid pressure $\Delta P_b$ and obtain the AC part of a displacement $\Delta \lambda_s'(n)$;

computing the AC part of the fluid pressure $\Delta P_b'(n)$ according to the impedance of the elastic tube $Z_{v2}(n)$ and the AC part of the displacement $\Delta \lambda_s'(n)$;

adding the DC part of the fluid pressure $\overline{P}_b'(n)$, which is equal to the DC part of the sensor's pressure $\overline{P}_s$, to the AC part of the fluid pressure $\Delta P_b'(n)$, to compute the real-time continuous fluid pressure $P_b(n)$;

extracting a series of equivalent mechanical properties including mass $M_v(n)$, damping $D_v(n)$, and stiffness $K_v(n)$ from the dynamic impedance of elastic tube $Z_{v2}(n)$ by using a parameter identification technique, and computing the dynamic compliance of elastic tube $C_v(n)$ using the reciprocal of the stiffness $K_v(n)$.

2. The method of claim 1, wherein the prediction measure is a spline curve fitting technique.

3. The method of claim 1, wherein the elastic tube to be measured is an arterial blood vessel, the surrounding tissues are muscle tissues, and the fluid pressure is a blood pressure in the arterial blood vessel.

4. The method of claim 1, wherein the detection head includes the DC-driven actuator, the AC-driven actuator, a DC displacement sensor, an AC displacement sensor, and a pressure sensor, the AC-driven actuator disposed in the DC-driven actuator and independently movable up and down relative to the DC-driven actuator, and the pressure sensor positioned on the end face of the AC-driven actuator so as to contact the surfaces of the surrounding tissues;

wherein the detection head is disposed within an applied measuring device, the device also including a control unit used for analyzing and processing signals, the control unit respectively connected with the two actuators, the two displacement sensors, and the pressure sensor electrically;

wherein the DC-driven actuator maintains the DC part of the sensor's pressure $\overline{P}_s$ on the surface of the surrounding tissues as equal to the DC part of the fluid pressure $\overline{P}_b$ in accordance with a DC control gain $G_d$, which is processed by a DC controller, and the displacement of the DC-driven actuator is measured by the DC displacement sensor;

wherein the AC-driven actuator moves up and down along with the AC part of the fluid pressure $\Delta P_b$ in the elastic tube in accordance with the AC control gain $G_a$, which is processed by an AC controller, and the displacement change $\Delta \lambda_s'$ of the AC-driven actuator is measured by the AC displacement sensor;

wherein the pressure sensor is used to measure the pressure on the surface of the surrounding tissues $P_s$ while pressing down the DC-driven actuator to maintain the DC part of fluid pressure $\overline{P}_b$ and moving the AC-driven actuator up and down to track the AC part of the fluid pressure $\Delta P_b$; and wherein the measured pressure signals are transmitted to the control unit for signal processing.

* * * * *